(12) United States Patent
Manzke et al.

(10) Patent No.: US 7,526,062 B2
(45) Date of Patent: Apr. 28, 2009

(54) COMPUTER TOMOGRAPHY METHOD FOR PERIODICALLY MOVING OBJECTS

(75) Inventors: Robert Manzke, Husberg (DE); Dominic J. Heuscher, Aurora, OH (US); Michael Grass, Buchholz in der Nordheide (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 230 days.

(21) Appl. No.: 10/596,151

(22) PCT Filed: Nov. 26, 2004

(86) PCT No.: PCT/IB2004/052567

§ 371 (c)(1),
(2), (4) Date: Jun. 1, 2006

(87) PCT Pub. No.: WO2005/055828

PCT Pub. Date: Jun. 23, 2005

(65) Prior Publication Data
US 2007/0140411 A1 Jun. 21, 2007

(30) Foreign Application Priority Data
Dec. 8, 2003 (EP) .................................. 03104581

(51) Int. Cl.
*A61B 6/03* (2006.01)
(52) U.S. Cl. .................. 378/8; 378/4; 378/901
(58) Field of Classification Search ............ 378/4, 378/8, 901
See application file for complete search history.

(56) References Cited

U.S. PATENT DOCUMENTS 5,991,356 A 11/1999 Horiuchi et al.
6,381,487 B1 * 4/2002 Flohr et al. ............... 600/425
6,504,894 B2 1/2003 Pan et al.
6,510,337 B1 1/2003 Heuscher et al.

(Continued)

FOREIGN PATENT DOCUMENTS

WO WO 02/103639 A2 * 12/2002

OTHER PUBLICATIONS

Taguchi et al., High temporal resolution for multislice helical computed tomography, 2000, Medical Physics, vol. 27, No. 5, pp. 861-872.*

(Continued)

*Primary Examiner*—Edward J Glick
*Assistant Examiner*—John M Corbett

(57) ABSTRACT

The invention relates to a computer tomography method, in which a periodically moving object, especially a heart, is irradiated by a beam bundle. In that process, intermediate images of one and the same subregion of the object are reconstructed using measured values from time intervals from different periods. That is, in each case exactly one period can be allocated to each intermediate image. The time intervals in the individual periods are adjusted in such a way that, after a reconstruction of the intermediate images using measured values that lie in the adjusted time intervals, a similarity measure applied to the intermediate images of the same subregion is minimized. This method can be applied to one, several or all subregions of the object that are reconstructable using measured values from time intervals from different periods. Finally, a computer tomography image is reconstructed, wherein exclusively measured values from the adjusted time intervals are used.

20 Claims, 6 Drawing Sheets

U.S. PATENT DOCUMENTS

Figure 1:
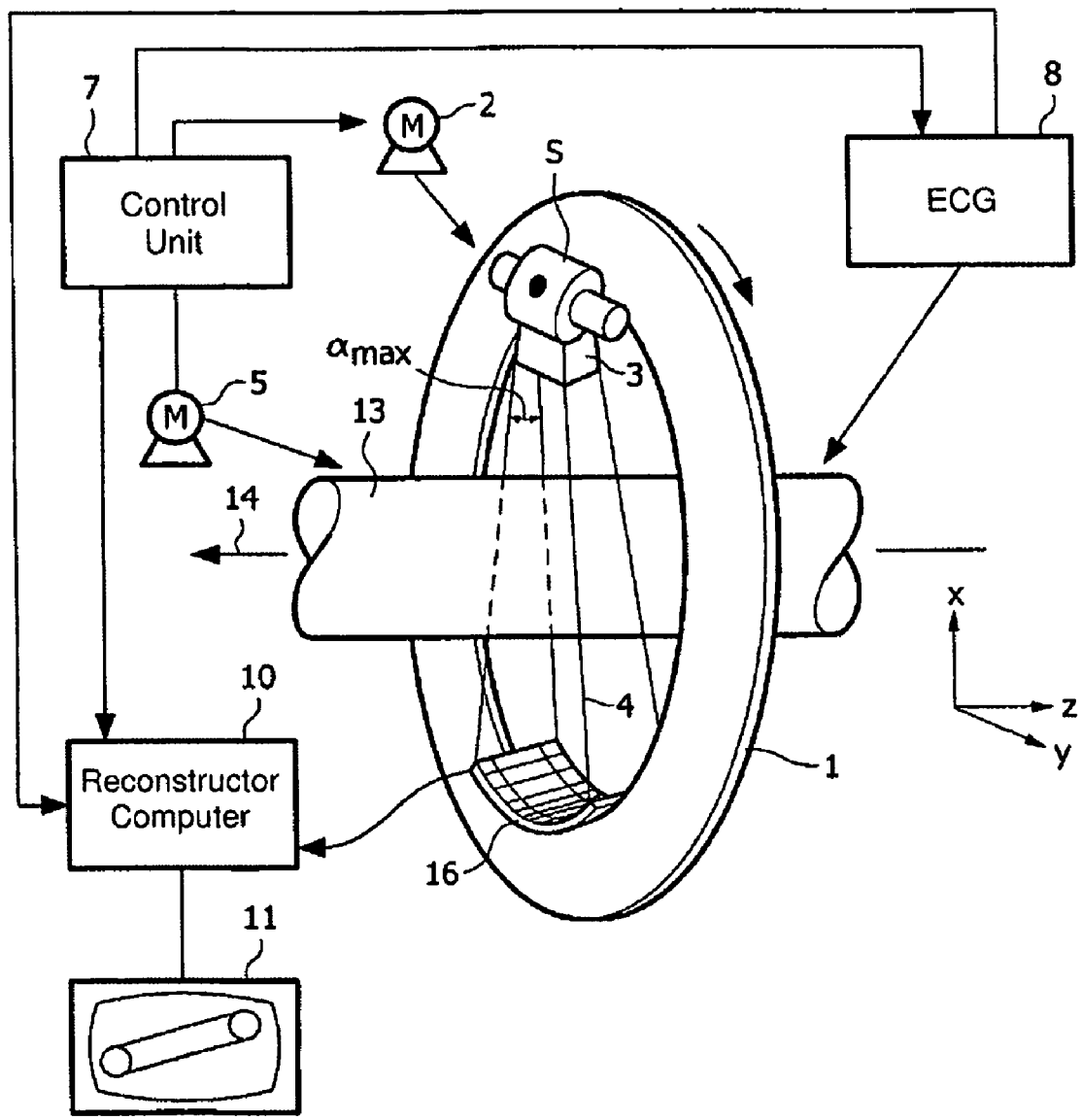

| | | | |
|---|---|---|---|
| 6,526,117 B1 * | 2/2003 | Okerlund et al. | 378/8 |
| 6,529,575 B1 * | 3/2003 | Hsieh | 378/4 |
| 6,539,074 B1 | 3/2003 | Yavuz et al. | |
| 6,628,743 B1 * | 9/2003 | Drummond et al. | 378/8 |
| 6,819,736 B1 | 11/2004 | Bruder et al. | |
| 2001/0043671 A1 * | 11/2001 | Grass et al. | 378/210 |
| 2002/0025017 A1 | 2/2002 | Stergiopoulos et al. | |
| 2002/0136438 A1 * | 9/2002 | Breeuwer | 382/128 |
| 2003/0007593 A1 | 1/2003 | Heuscher et al. | |
| 2003/0072419 A1 * | 4/2003 | Bruder et al. | 378/210 |
| 2003/0092983 A1 | 5/2003 | Baker et al. | |

OTHER PUBLICATIONS

Grass et al., A Projection-Based Method for Motion-Compensated Noise Suppression, 1998, Philips J. Res., pp. 283-298.*

Grass et al., Automatic Phase Point Determination for High-Resolution Cardiac CT Reconstruction, Dec. 1, 2003, RSNA 2003, Abstract code E08-462.*

Brown, A Survey of Image Registration Techniques, 1992, ACM Computing Surveys, vol. 24, No. 4, pp. 325-376.*

Vembar, M., et al.; A dynamic approach to identifying desired physiological phases for cardiac imaging using multislice spiral CT; 2003; Med. Phys.; 30(7)1683-1693.

* cited by examiner

COMPUTER TOMOGRAPHY METHOD FOR PERIODICALLY MOVING OBJECTS

The invention relates to a computer tomography method, in which a periodically moving object, especially a heart, is irradiated by a beam bundle. The invention relates in addition to a computer tomograph for carrying out the method and to a computer program for controlling the computer tomograph.

In known methods of the kind mentioned at the beginning, the three-dimensional spatial course of the absorption or the attenuation of the radiation in the periodically moving object is reconstructed from measured values that are acquired using a detector unit. During that process, the effect of the periodic movement of the object is that the measured values contain information from different object states, which in turn leads to movement artifacts in the reconstructed data record.

In order to reduce these movement artifacts, during the acquisition of measured values in known methods, movement signals, for example an electrocardiogram, dependent on the movement of the object, are recorded, so that a movement signal can be allocated to each measured value. Only measured values to which identical or only slightly differing movement signals are allocated are then used for the reconstruction.

The disadvantage of this method is that identical movement signals do not as a rule correspond to identical object states. The measured values used for reconstruction may have been allocated substantially identical movement signals, but this does not mean that they have also been allocated substantially identical object states. The above-described selection of the measured values used for reconstruction therefore also leads to very marked movement artifacts.

It is an object of the present invention to specify a computer tomography method, a computer tomograph and a computer program, with which these movement artifacts are less marked.

That object is achieved in accordance with the invention by a computer tomography method having the following steps:
a) generation by a beam source of a beam bundle passing through a periodically moving object,
b) generation of a relative movement between the beam source on the one hand and the object on the other hand, which comprises a rotation about an axis of rotation,
c) acquisition by means of a detector unit, during the relative movement, of measured values that are dependent on the intensity in the beam bundle on the other side of the object, an acquisition time being allocated to each measured value and to the beam causing the respective measured value,
d) detection of a movement signal depending on the movement of the object by means of a movement-detection device and determination of periods of the periodic movement by means of the detected movement signal,
e) reconstruction of a computer tomography image of the object from the measured values, wherein there are used only measured values whose acquisition times lie within the periods ($T_1 \ldots T_7$) at time intervals ($\Delta t_1 \ldots \Delta t_7; \Delta t'_1 \ldots \Delta t'_7$), which are so determined that a similarity measure applied to intermediate images of the same subregion (23; 25) of the object is minimized, wherein different intermediate images are reconstructed using measured values from time intervals ($\Delta t_1 \ldots \Delta t_7; \Delta t'_1 \ldots \Delta t'_7$) from different periods ($T_1 \ldots T_7$).

Intermediate images of one and the same subregion are thus reconstructed using measured values from time intervals from different periods. That is, in each case exactly one period can be allocated to each intermediate image. The time intervals in the individual periods are now adjusted in such a way that, after a reconstruction of the intermediate images with the adjusted time intervals, a similarity measure applied to the intermediate images of the same subregion is minimized. This method can be applied to one, several or all subregions of the object that are reconstructable using measured values from time intervals from different periods. Finally, a computer tomography image is reconstructed, wherein exclusively measured values from the adjusted time intervals are used.

The movement artifacts described in the beginning occur particularly noticeably in the regions of the reconstructed image that were reconstructed using measured values from time intervals from different periods. That is why it is important especially in these regions to use for the reconstruction measured values that were acquired during the time the object was in object states as identical as possible. This is achieved in accordance with the invention by determining the corresponding time intervals so that a repeated reconstruction of the relevant subregion, in each case using measured values from different periods, leads to images as similar as possible. The subsequent reconstruction of the computer tomography image using all measured values that lie in the time intervals thus determined leads to a computer tomography image (CT-image) having fewer marked movement artifacts compared with the prior art.

The term "periodic movement" is not restricted to a periodicity in the exact sense, that is, it is not restricted to movements in which object states regularly recur exactly, i.e. exactly identical object states at exactly equidistant instants. A periodic movement within the scope of the invention includes in particular movements that differ from a mathematical exactness, as is known in the case of periodically moving body organs, for example, the heart. That is, similar, substantially identical object states are passed through at instants that as a rule are substantially equidistant.

Subregion as used herein can also be a region to be reconstructed, which comprises the entire object or just a portion of the object.

The description herein includes methods in which each two consecutive periods form a period pair and a first intermediate image of a subregion is reconstructed exclusively using measured values whose acquisition instants lie in the time interval of the earlier period of a period pair, and a second intermediate image of the same subregion is reconstructed exclusively using measured values whose acquisition instants lie in the time interval of the later period. The intermediate images are compared with the similarity measure. The reconstruction of one of the intermediate images is now carried out with modified, especially shifted, time intervals until a break-off criterion dependent on the similarity measure is satisfied. This leads to a further reduction in movement artifacts.

Also described herein is break-off criterion and a similarity measure, which produce a reconstructed CT image of very good quality.

In some of the embodiments, each measured value is weighted before the reconstruction, which leads to a further improvement in the image quality.

Also described are computer tomography methods in which use is made of a filtered back-projection respectively a lower three-dimensional resolution in the reconstruction of the intermediate images than in the reconstruction of the CT image, thus reducing the computing expenditure.

Some embodiments use an electrocardiogram as movement signal. This leads to a CT image of a beating heart with only few movement artifacts.

A computer tomograph for carrying out the method described herein.

Another embodiment defines a computer program for controlling a computer tomograph.

These and other aspects of the invention are apparent from and will be elucidated with reference to the embodiments described hereinafter.

Figure 2:
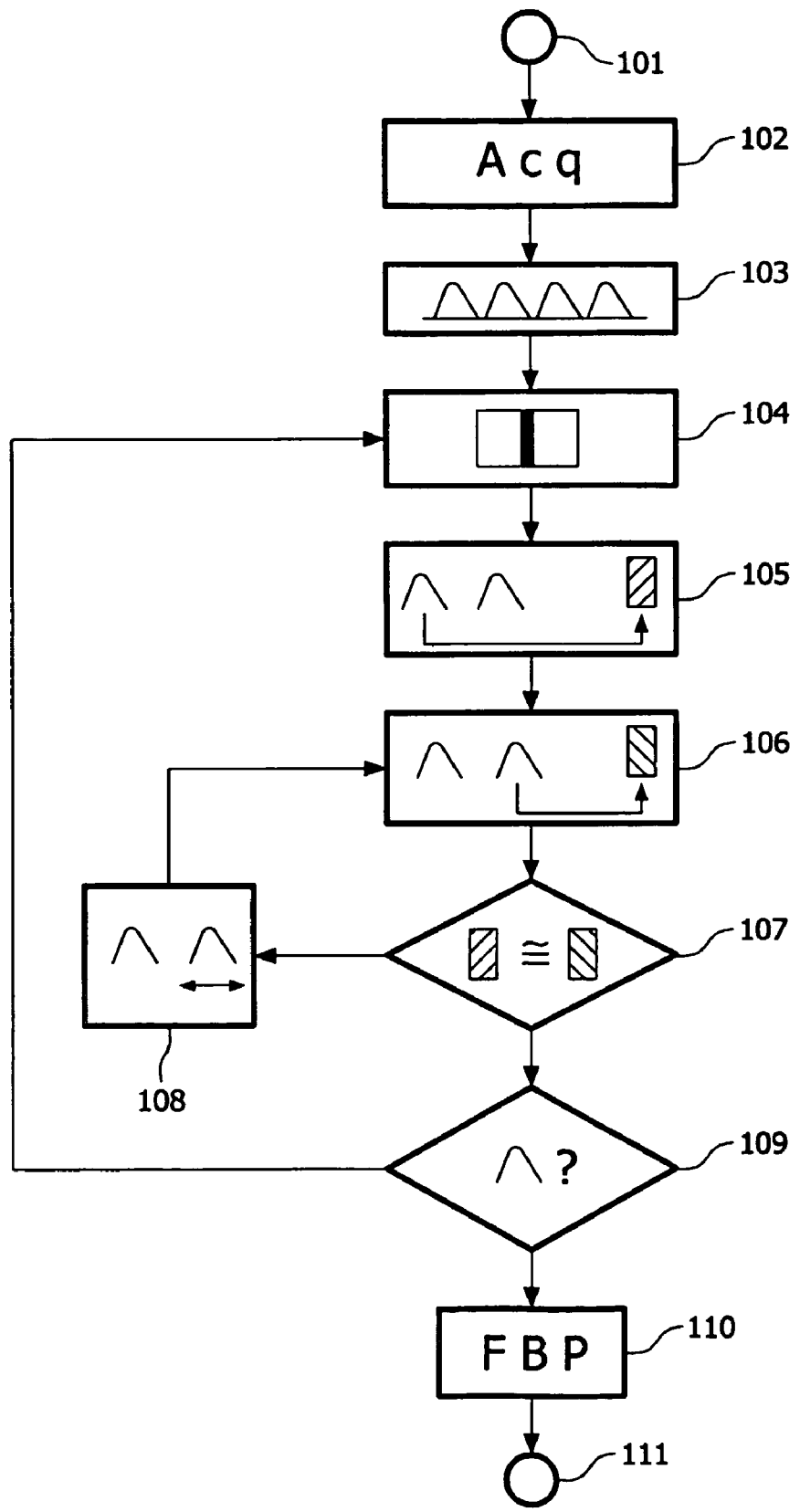
Figure 3:
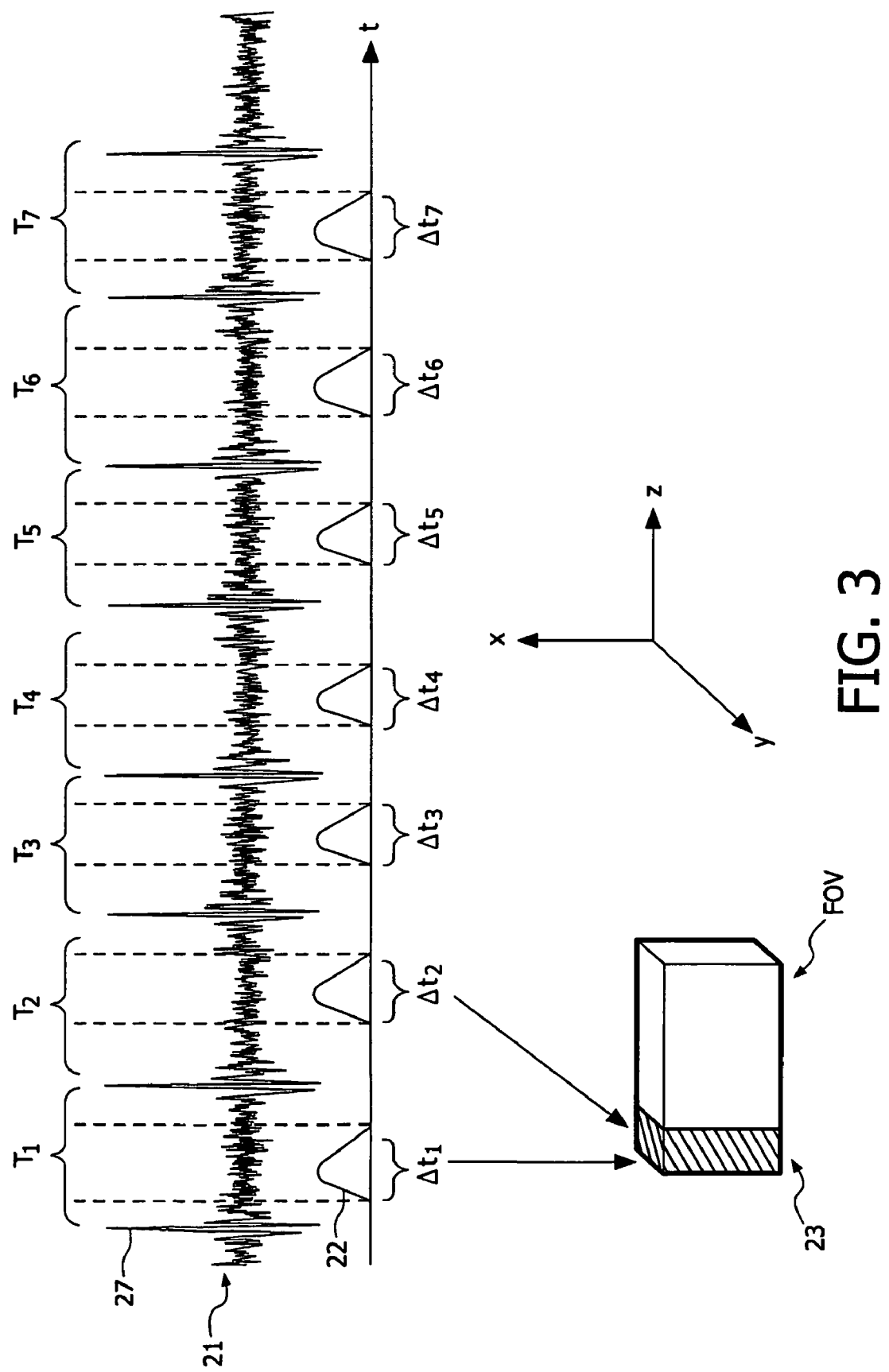
Figure 4:
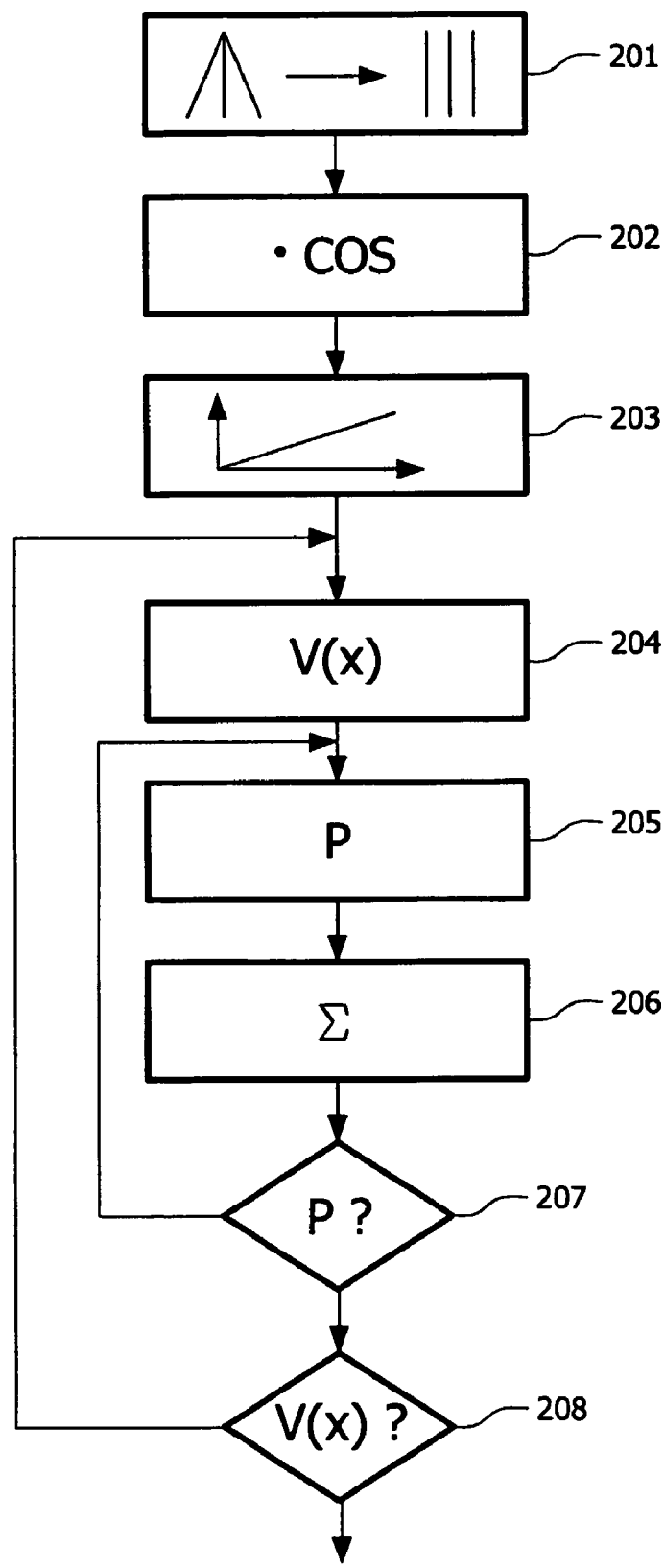
Figure 5:
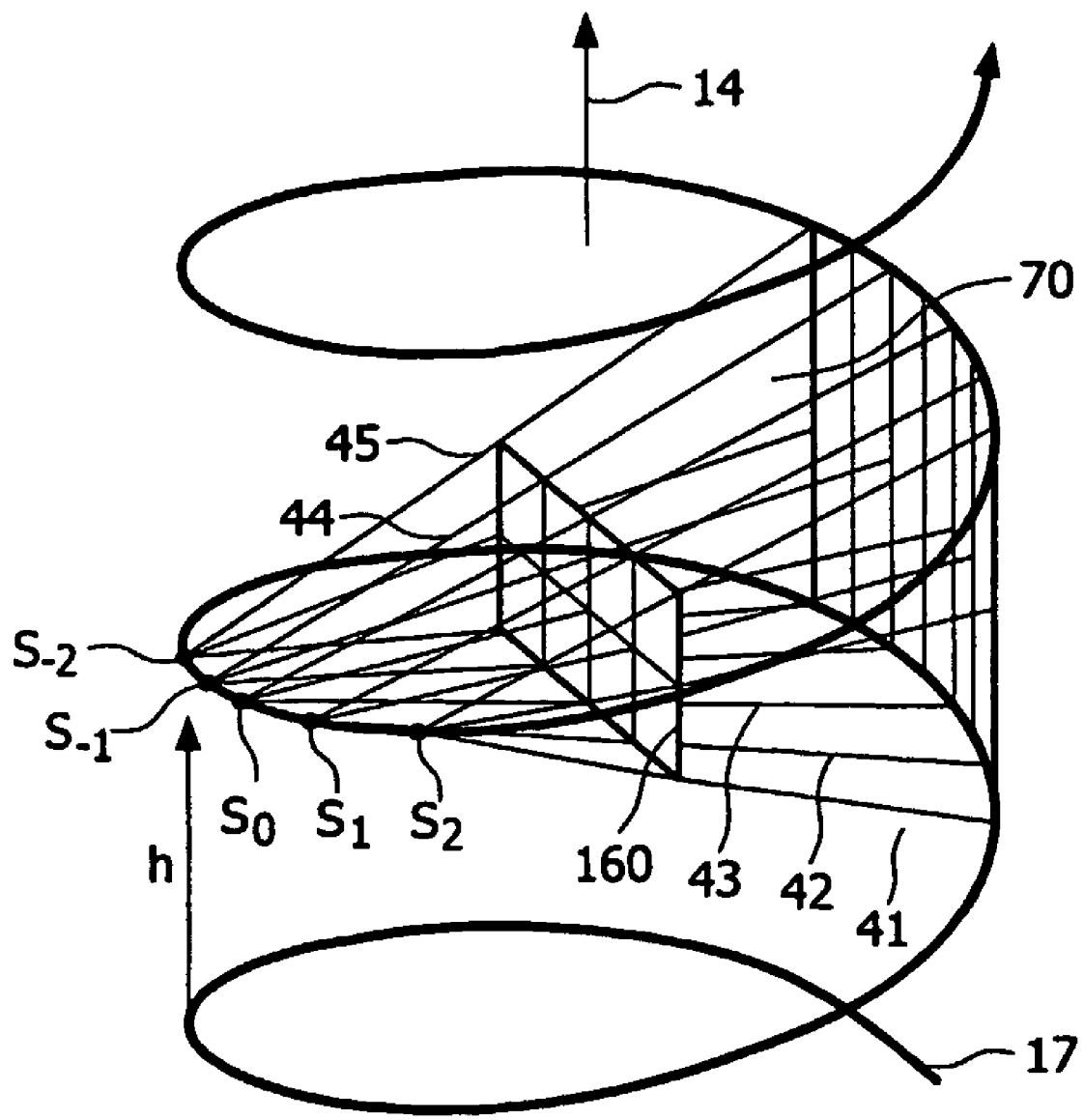
Figure 6:
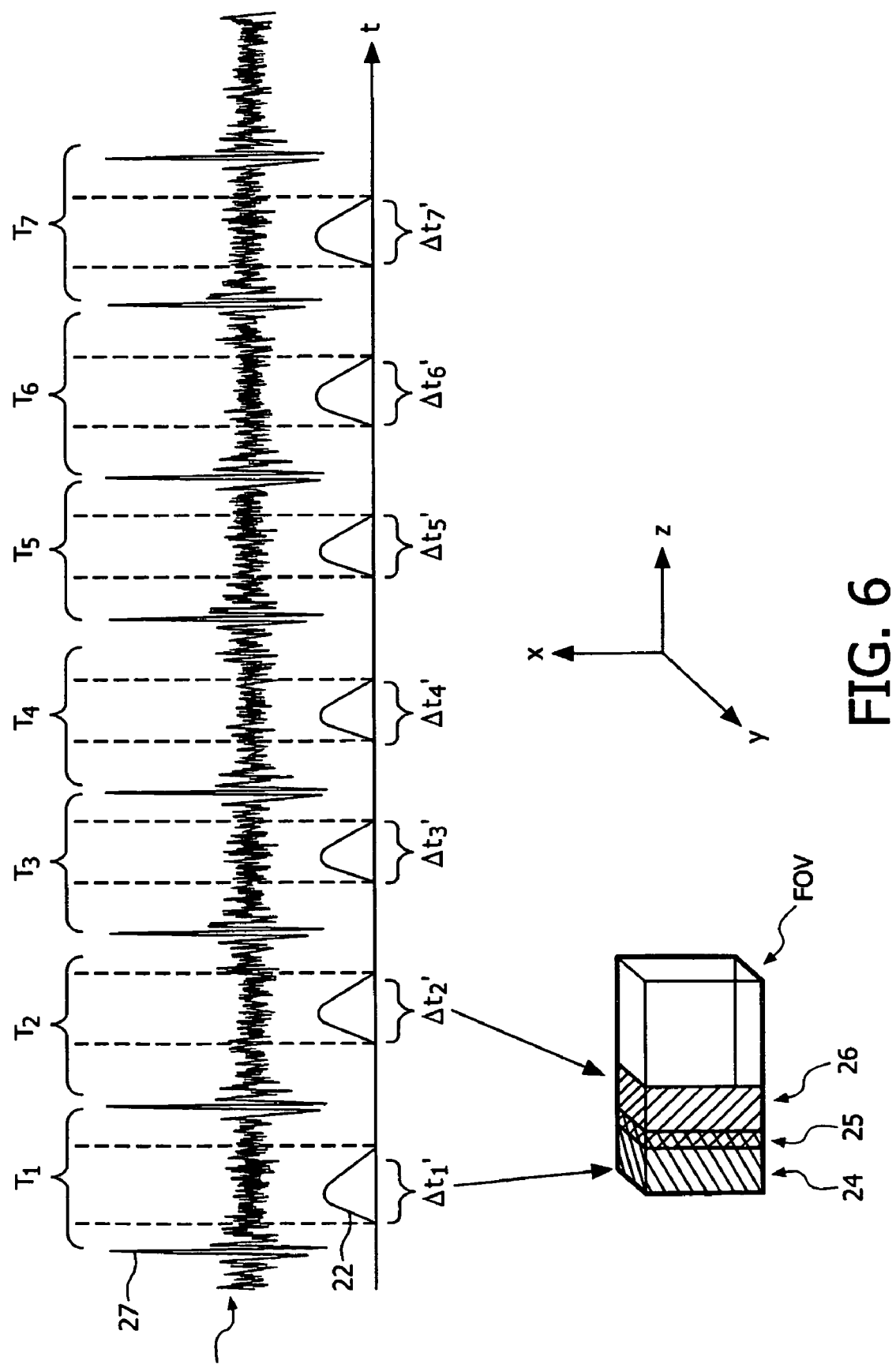

In the drawings:

FIG. 1 shows a computer tomograph, with which the method according to the invention can be implemented, FIG. 2 is a flow chart of the method according to the invention, FIG. 3 shows a schematic representation of a correlation between periods, time intervals and reconstructed object regions, FIG. 4 is a flow chart of a filtered back-projection, FIG. 5 shows a schematic perspective view of a helical trajectory, a virtual detector and several beam fans, and FIG. 6 shows a further schematic representation of a correlation between periods, time intervals and reconstructed object regions.

The computer tomograph shown in FIG. 1 comprises a gantry 1, which is capable of rotating about an axis of rotation 14 running parallel to the z-direction of the coordinate system illustrated in FIG. 1. For that purpose, the gantry 1 is driven by a motor 2 at a preferably constant, adjustable angular velocity. A beam source S, for example an X-ray tube, is fixed to the gantry 1. The X-ray tube is provided with a collimator arrangement 3, which from the radiation produced by the beam source S extracts a conical beam bundle 4, i.e. a beam bundle that has a finite extent other than zero both in the z-direction and in a direction perpendicular thereto (i.e. in a plane perpendicular to the axis of rotation). Alternatively, a fan-shaped beam could be used.

The beam bundle 4 passes through a cylindrical examination region 13, in which a periodically moving object (not illustrated) is located. In this exemplary embodiment this object is a beating heart, which performs proper motion and is possibly additionally moved back and forth by respiratory motion of the patient. In other embodiments, other periodically moving body parts, such as the liver, brain or arteries, or periodically moving technical objects could alternatively be irradiated.

After passing through the examination region 13, the beam bundle 4 impinges on a detector unit 16 fixed to the gantry 1, the detector unit having a detector surface comprising a plurality of detector elements, which in this embodiment are arranged matrix-form in rows and columns. The detector columns extend preferably parallel to the axis of rotation 14. The detector rows are located in planes perpendicular to the axis of rotation, in this embodiment on an arc of a circle around the beam source S (focus-centered detector). In other embodiments they could alternatively be of a different form, for example, they could describe an arc of a circle about the axis of rotation 14 or be linear. Each of the detector elements on which the beam bundle 4 impinges supplies in each position of the beam source a measured value for a beam from the beam bundle 4. If in other embodiments a fan-shaped beam bundle is used, then the detector unit could alternatively have just a single row of detectors.

The angle of aperture of the beam bundle 4 denoted by $\alpha_{max}$ determines the diameter of the object cylinder, within which the object to be examined is located during acquisition of the measured values. The angle of aperture is here defined as the angle that a ray lying in a plane perpendicular to the axis of rotation 14 at the edge of the beam bundle 4 encloses with a plane defined by the beam source S and the axis of rotation 14. The examination region 13 or rather the object, or the patient support table, can be displaced by means of a motor 5 parallel to the axis of rotation 14 and the z-axis. Alternatively and equivalently, the gantry could be displaced in that direction. If the object is a technical object and not a patient, the object can be rotated during an examination, whilst the beam source S and the detector unit 16 remain stationary.

By means of the motors 2 and 5, the beam source S and the detector unit 16 are able to describe a trajectory relative to the examination object 13, this trajectory running on a notional cylinder surface. This trajectory can run, for example, helically, when both motors are in operation. If, however, the motor 5 for advance in the direction of the axis of rotation 14 is idle, and the motor 2 allows the gantry to rotate, a circular trajectory is produced for the beam source S and the detector unit 16 relative to the examination region 13. In the present embodiment, the helical trajectory will be considered.

During acquisition of the measured values, the cardiac motion is recorded in known manner by means of an electrocardiograph 8. For that purpose the thoracic region of a patient is connected by means of electrodes (not illustrated) to the electrocardiograph 8. Alternatively, the pulse could be used as the movement signal describing the cardiac motion. In other embodiments, especially in the case of other moving objects, the motion of the object can be followed by means of other movement signals. Thus, for example, in the case of a technical object that is periodically moved by a motor, a signal of the motor is used as movement signal.

In the present embodiment, it is assumed that the patient is not breathing during the measurement. The respiratory motion can therefore be disregarded. Alternatively, the respiratory motion could be measured, for example, using a deformable abdominal belt that is connected to a respiratory motion-measuring device.

The measured values acquired from the detector unit 16 are fed to a reconstruction unit, especially a reconstruction computer 10, which is connected to the detector unit 16, for example, via a contactlessly operating data transmission (not illustrated). In addition, the electrocardiogram is transmitted from the electrocardiograph 8 to the reconstruction unit 10. The reconstruction unit 10 reconstructs the absorption distribution in the examination region 13 and reproduces it, for example, on a monitor 11. The two motors 2 and 5, the reconstruction unit 10, the beam source S, the electrocardiograph 8, the transmission of the measured values from the detector unit 16 to the reconstruction unit 10 and the transmission of the electrocardiogram from the electrocardiograph 8 to the reconstruction unit 10 are controlled by the control unit 7.

In other embodiments, the acquired measured values and the measured electrocardiograms for reconstruction can first be fed to one or more reconstruction computers, which forward the reconstructed data, for example, via a fiber optic cable, to an image-processing computer.

FIG. 2 shows the sequence of a measuring and reconstructing method that can be implemented with the computer tomograph as shown in FIG. 1.

After initialization in step 101, the gantry rotates at an angular velocity that in this embodiment is constant, but can alternatively vary, for example, in dependence on time or on the position of the beam source.

In step 102, the examination region or rather the object, or the patient support table, is displaced parallel to the axis of rotation and the radiation of the beam source S is switched on so that the detector unit 16 is able to detect the radiation from a plurality of angular positions. At the same time, or even before the beam source S is switched on, the electrocardiograph 8 is activated, so that an electrocardiogram 21 (FIG. 3) is measured simultaneously.

In the present embodiment, the beam source S moves on a helical trajectory relative to the examination region 13. Alternatively, the beams source S could move along an arbitrary trajectory running on a notional cylinder surface, for example, along a circular trajectory.

In step 103, periods $T_1 \ldots T_7$ are determined by means of the electrocardiogram 21 (see FIG. 3). A period in this embodiment is defined by the distance in time between two adjacent R-peaks 27 of the electrocardiogram 21. Furthermore, initially in each period $T_1 \ldots T_7$ a time interval $\Delta t_1 \ldots \Delta t_7$ is determined. Although the index for the periods and the time intervals runs only from 1 to 7, the number of periods and time intervals is naturally not restricted to this number. On the contrary, the method according to the invention can be carried out with an arbitrary number of periods and time intervals.

The initial determination of the time intervals $\Delta t_1 \ldots \Delta t_7$ can be effected in different ways. For example, time intervals of which it is known that the heart moves less in these time intervals than in other time intervals can be predetermined. Thus, it is known that a human heart moves relatively little in a time interval that lies between 65% and 85% of the time range between two adjacent R-peaks.

Alternatively, for initial determination of time intervals in which an object moves as little as possible, in the first instance a 4D-data set with a low resolution (e.g. 20×20×20 cm$^3$ represented by 64$^3$ voxels) could be reconstructed, for example by means of a filtered back-projection. The 4D-data set contains several CT images of the region of the object to be reconstructed (FOV—field of view). Each of these CT images was reconstructed exclusively using measured values whose acquisition instants lie in time intervals that are identically arranged within the respective period. That is to say, the first CT image has, for example, been reconstructed exclusively using measured values whose acquisition instants lie in time intervals whose midpoints are arranged at a point denoted by 5% RR within the respective period. The second CT image has been reconstructed, for example, exclusively using measured values whose acquisition instants lie in time intervals whose midpoints are arranged at a point denoted with 10% RR within the respective period, and so on.

The time intervals that contain acquisition instants of the measured values with which the respective CT images have been reconstructed can therefore be arranged staggered with respect to one another, for example, by 5% RR, in the respective period. The expression "x % RR" in this case denotes a phase point at the location $t=t_R+0.01 \times \Delta t_{RR}$, in which $t_R$ is the instant of the first R-peak of the respective period and $\Delta t_{RR}$ is the distance in time between the two R-peaks of the respective period. A phase point is therefore allocated to each CT image. Next, CT images having adjacent phase points (e.g. 5% RR and 10% RR) could then be compared with one another. For that purpose, for example, absolute differences of corresponding voxels of the CT images having adjacent phase points could be formed and added up, the CT images being more similar, the smaller is the resulting sum. The more similar two such compared CT images are, the less the object has moved between the corresponding phase points. The time intervals could therefore initially be set in the regions of a period in which two CT images having adjacent phase points are as similar as possible. If, for example, the CT images having the phase points 70% RR respectively 75% RR are most similar, then in each period the respective time interval could lie between 70% and 75% RR.

In addition, in step 103, in each initially fixed time intervals a weighting function 22 is defined. The weighting function serves to weight each measured value in a time interval before it is used for reconstruction of the object. The weighting function preferably progresses so that the measured values gain increasingly in importance the more they are arranged in the middle of the respective time interval.

The weighting function could alternatively be designed so that measured values that lie in a time interval are multiplied by 1 and measured values that lie outside the time intervals are multiplied by 0.

In step 104, adjacent periods are considered. At the first execution of step 104, first of all the chronologically first time interval $\Delta t_1$ of the time intervals initially fixed in step 103 is determined, which contains acquisition instants of measured values whose corresponding beams have irradiated the portion of the object to be reconstructed. The period $T_1$, in which the chronologically first time interval $\Delta t_1$ lies, and the subsequent period $T_2$ form the first period pair. When step 104 is next executed, the second period pair would be formed from the chronologically second period $T_2$ and the chronologically third period $T_3$, and so on. In this way, on each execution of step 104, corresponding to the chronological time sequence in each case a period pair is formed with periods adjacent in time.

The periods of a period pair and the corresponding time intervals are denoted in the following description by $T_1$, $T_2$ and $\Delta t_1$, $\Delta t_2$ respectively. These reference numerals, in conjunction with FIG. 3, serve to illustrate the following steps and do not, of course, mean that the following steps are restricted only to the chronologically first two periods and time intervals.

Furthermore, in step 102 the subregion 23 of the FOV traversed both by beams whose acquisition instants lie in the time interval $\Delta t_1$ of the one period $T_1$ of the period pair and by beams whose acquisition instants lie in the time intervals $\Delta t_2$ of the other period $T_2$ of the period pair is determined. Since the acquisition geometry, the acquisition times and the initial arrangement of the time intervals are known, this subregion 23 can be determined by (simple) geometric considerations or by computer simulations.

In step 105, the subregion 23 determined in step 104 is reconstructed only with measured values whose acquisition instants lie in the time interval $\Delta t_1$ of the one period $T_1$ of the current period pair, so that a first intermediate image is produced. This reconstruction can be carried out using known reconstruction techniques, such as filtered back-projection or iterative methods (e.g. ART—algebraic reconstruction technique), wherein, before the reconstruction, the measured values whose acquisition instants lie in the time interval $\Delta t_1$ are weighted in accordance with the weighting function 22. The filtered back-projection is explained in more detail below in conjunction with the final reconstruction of the entire CT image (see FIG. 4).

In step 106, a second intermediate image of the subregion 23 determined in step 104 is reconstructed using only measured values whose acquisition instants lie in the time interval $\Delta t_2$ of the other period $T_2$ of the current period pair. The reconstruction of this intermediate image is also not restricted to specific reconstruction methods. Moreover, here too the measured values are weighted in accordance with the weighting function 22 prior to reconstruction.

The reconstruction of the intermediate images can be carried out at a clearly lower resolution (e.g. 64$^3$ voxels for a region of 20×20×20 cm$^3$ to be reconstructed) compared with the later final reconstruction of the CT image.

A comparison of the two intermediate images takes place in step 107. For that purpose, a similarity measure is applied to the two intermediate images. Many similarity measures that compare two images with one another and produce a similarity value dependent on the degree of similarity are known. According to the invention, any such similarity measure can be used. Known similarity measures use, for example, differences or correlations. The similarity measure a can be formed, for example, by a mean value of the absolute differences of corresponding voxels:

$$\sigma = \frac{1}{N} \sum_i |V_{1,i} - V_{2,i}| \quad (1)$$

with $i = 1, \ldots, N$.

Here, N is the number of voxels in one of the intermediate images, $V_{1,i}$ is the image value of the i-$^{th}$ voxel of the first intermediate image and $V_{2,i}$ is the image value of the i-$^{th}$ voxel of the second intermediate image. Furthermore, the mean quadratic deviation of corresponding voxels could also be used as similarity measure:

$$\sigma = \frac{1}{N} \sum_i \sqrt{(V_{1,i} - V_{2,i})^2} \quad (2)$$

with $i = 1, \ldots, N$.

If the similarity measure yields a similarity value that is less than a predetermined threshold value, then step 109 is continued. Otherwise step 108 follows.

In step 108, the time interval $\Delta t_2$ of the later period $T_2$ of the period pair is modified. It can be shifted, the width of the time interval can be reduced or enlarged and/or the course of the weighting function can be varied. For example, upon each execution of step 108 the time interval $\Delta t_2$ can be shifted in one direction by a pre-determinable distance of time. Thus, at the first execution the time interval $\Delta t_2$ can be shifted by once the distance of time in the direction of shorter times, during the next execution by twice the distance of time in the direction of longer times, then by three times the distance of time in the direction of shorter times and so on. What matters is that upon each execution the time interval $\Delta t_2$, and possibly also the weighting function, are modified.

After the time interval $\Delta t_2$ of the later period $T_2$ of the period pair has been modified, in step 106 the subregion 23 determined in step 104 is reconstructed once again using measured values whose acquisition instants lie in the modified time interval $\Delta t_2$. The resulting new second intermediate image is compared in step 107 by means of a similarity measure with the first intermediate image. When the similarity measure yields a similarity value that lies above the similarity threshold, then the time interval $\Delta t_2$ of the later period $T_2$ of the period pair is modified once again in step 108. This time interval $\Delta t_2$ is therefore modified until the similarity measure yields a similarity value that is less than the similarity threshold. The outcome of this is that, after the similarity threshold is reached, the two intermediate images are relatively similar. This means that the object states that are represented by the two intermediate images are also relatively similar. As will be explained in detail below, this leads to a reduction in the movement artifacts in the finally reconstructed CT image.

Alternatively, in step 106 the subregion 23 determined in step 104 could also be reconstructed repeatedly using measured values from different time intervals $\Delta t_2$ of the later period $T_2$ of the period pair. The different time intervals $\Delta t_2$ can be arranged close to the initial time interval but slightly staggered with respect thereto. The several resulting second intermediate images could then each be compared in step 107 with the first intermediate image by means of the similarity measure, wherein that particular second intermediate image (or rather that particular time interval $\Delta t_2$ of the later period $T_2$) that together with the first intermediate image leads to the smallest similarity value, is selected.

The invention is not restricted to the determination described here of the time intervals by means of period pairs. On the contrary, in place of step 104 to 109 it is possible according to the invention to apply any method that adjusts the time intervals in the periods so that a similarity measure applied to several intermediate images of the same subregion is minimized, wherein different intermediate images have been constructed using measured values from different periods and from only one period in each case. For that purpose, all subregions that are reconstructable using measured values from different periods can be determined. Since an intermediate image is reconstructed for each period, the number of intermediate images of a subregion is equal to the number of periods whose time intervals contain measured values with which the corresponding subregion is reconstructable. The time intervals in the periods are now modified until a similarity measure applied to intermediate images of the modified time intervals is minimized. This method can be carried out for each subregion that is reconstructable using measured values from different periods.

Step 109 tests whether all periods containing acquisition instants of beams that have traversed the FOV have already been taken into account. If that is not the case, then step 104 is continued. Otherwise, step 110 follows.

In step 110, a CT image of the entire FOV is reconstructed, wherein the measured values are beforehand weighted in accordance with the respective weighting function 22, if this has not already taken place, and wherein only measured values whose acquisition instants lie in the time intervals determined in steps 103 to 109 are used. Since the time intervals have been determined in such a way that the intermediate images that represent the same subregion of the object, yet have been reconstructed with measured values from different periods, are very similar, the object states that are represented by these intermediate images are also very similar. If now, as in step 110, measured values from different periods are used for reconstruction of such a subregion, then the movement artifacts in these subregions are reduced in comparison with known methods.

In the reconstruction of periodically moving objects it is naturally advantageous if the time resolution in the CT images is as high as possible. A high resolution can be achieved by selecting time intervals in the periods that are as narrow as possible. In order still to obtain a sufficient number of measured values for the reconstruction of a good quality CT image, each subregion of the FOV must be traversed by beams whose acquisition instants lie in different periods. In the case of known methods, this leads to marked movement artifacts, since as a rule the same object state is not found in every period. According to the invention, the time intervals in the periods are, however, selected so that the above-mentioned intermediate images and hence also the corresponding object states are as similar as possible. The method according to the invention therefore leads to reconstructed CT images having a high time resolution and reduced movement artifacts in comparison with the prior art.

According to the invention, any reconstruction method can be used in step 110 for the reconstruction of the CT image. For preference, a kind of filtered back-projection is carried out, which is illustrated by means of a flow chart in FIG. 4.

For reconstruction, in step 201 the measured values are re-grouped in parallel. The measured values are re-sorted and re-interpolated by the parallel re-grouping as though they had been measured with a different beam source (an expanded beam source, which is arranged on a part of a helix and is able to emit beam fans parallel with one another) and with a different detector (a flat, rectangular "virtual detector" containing the axis of rotation 14).

This is explained in detail with reference to FIG. 5. The reference numeral 17 here denotes the helical trajectory from which the beam source irradiates the examination region. A fan-shaped beam bundle 43, the beams of which run in a plane containing the axis of rotation 14, is emitted from the beam source position $S_0$. The conical beam bundle, which is emitted from the beam source in the position $S_0$, can be envisaged as comprising a plurality of flat beam fans that are located in planes parallel to the axis of rotation 14 and intersect at the beam source position $S_0$. FIG. 5 shows just a single one of these beam fans, namely the beam fan 43.

In addition, FIG. 5 illustrates yet further beam fans 41, 42 and 44, 45, which are parallel to the beam fan 43 and lie in planes parallel to one another and to the axis of rotation 14. The associated beam source positions $S_{-2}$, $S_{-1}$ and $S_1$, $S_2$ are assumed by the beam source S before respectively after it has reached the beam source position $S_0$.

The beam fans 41 to 45 form a group and define a beam bundle 70 having a tent-like form. A group of beam fans is called a projection. For each projection a rectangular virtual detector 160 is now defined which lies in a plane that contains the axis of rotation 14 and is oriented perpendicular to the parallel beam fans of a projection. The corner points of the virtual detector 160 are the penetration points through that plane of the beams that from the outer beam source positions meet the opposing portion of the helix. For the ray bundle 70 in FIG. 5, $S_{-2}$, and $S_2$ are the outer beam source positions. Detector elements arranged in accordance with Cartesian geometry, that is, rows and columns, on which the measured values are re-interpolated, are defined on the rectangular detector 160.

In step 202, the measured values associated with the individual beams are subsequently multiplied with a weighting factor that corresponds to the cosine of the cone angle of the respective beam. The cone angle of a beam is the angle that this beam encloses with a plane that is oriented perpendicular to the axis of rotation 14. If said angle is small, then the cosine of the angle is substantially equal to 1, so that step 202 can be omitted.

In step 203, a one-dimensional filtering with a transmission factor increasingly linearly with the spatial frequency is applied to the measured values. For that purpose, in each case consecutive values in the direction perpendicular to the axis of rotation 14, that is, along a line of the detector 160, are used. This filtering is performed along each line of the virtual detector for all groups of beam fans.

In another embodiment, the parallel re-grouping could be omitted. Then, as is known, since the detector unit is e.g. curved in an arc around the beam source or around the axis of rotation, the filtering must be modified.

In step 204, a voxel V(x) inside the FOV is determined. Then, in step 205, a projection, that is, a group of beam fans, which has not yet been used for reconstruction of the voxel V(x) and whose acquisition instant lies in one of the above-determined time intervals, is selected. If no beam of the projection runs centrally through the voxel V(x), then it is ascertained at which point a central beam would meet the detector surface. The associated measured value is then calculated by interpolation of the measured values of adjacent beams. The measured value that can be allocated to the beam of the projection passing the voxel, or rather the corresponding measured value obtained by interpolation, is accumulated in step 206 on the voxel V(x). Step 208 tests whether all projections have been taken into account. If this is not the case, then the flow chart branches to step 205. Otherwise, step 208 tests whether all voxels V(x) in the FOV have been passed through. If this not the case, then step 204 is continued. If, on the other hand, all voxels V(x) in the FOV have been passed through, then the absorption in the FOV as whole is determined and the computer tomography method according to the invention ends with step 111 (see FIG. 2).

In the reconstruction of the CT image, steps 201 to 203 can be omitted if the measured values have already been appropriately processed during the reconstruction of the intermediate images in steps 105 and 106.

The method according to the invention is independent of whether the entire FOV comprises subregions that are traversed by beams whose acquisition instants lie in different periods, or of whether only parts of the FOV have these subregions. The latter case is illustrated in FIG. 6.

In FIG. 6 a subregion 24 of the FOV has been reconstructed with measured values whose acquisition instants lie in a time interval $\Delta t'_1$ of the period $T_1$. An adjacent subregion 26 of the FOV has been reconstructed with measured values whose acquisition instants lies in the time interval $\Delta t'_2$ in the following period $T_2$. Between these two subregions 24, 26 there is a subregion 25, which is traversed both by beams whose acquisition instants lie in the time interval $\Delta t'_1$ and by beams whose acquisition instants lie in the time interval $\Delta t'_2$. In order to minimize movement artifacts in the subregion 25, the time intervals $\Delta t'_2$, as described above in connection with steps 106 to 108, is modified, so that the similarity measure applied to intermediate images of the subregion 25, which in each case have been reconstructed exclusively with measured values from either the time intervals $\Delta t'_1$ or the time intervals $\Delta t'_2$, yields a minimized similarity value. The intermediate images are hence very similar, which leads to a reduction in movement artifacts in the CT image of the entire FOV to be reconstructed.

LIST OF REFERENCE NUMERALS

| | |
|---|---|
| h | Spacing of adjacent turns of a helical trajectory |
| S | Beam source |
| $S_{-2} \ldots S_2$ | Beam source position |
| $T_1 \ldots T_7$ | Periods |
| $\alpha_{max}$ | Angle of aperture |
| $\Delta t_1 \ldots \Delta t_7$; $\Delta t'_1 \ldots \Delta t'_7$ | Time intervals |
| 1 | Gantry |
| 2, 5 | Motor |
| 3 | Collimator arrangement |
| 4 | Beam bundle |
| 7 | Control unit |
| 8 | Electrocardiograph |
| 10 | Reconstruction unit |
| 11 | Monitor |
| 13 | Examination region |
| 14 | Axis of rotation |
| 16 | Detector unit |
| 17 | Helical trajectory |
| 21 | Electrocardiogram |
| 22 | Weighting function |
| 23 ... 26 | Subregion of the FOV |
| 27 | R-peak |
| 41 ... 45 | Beam fan |
| 70 | Beam bundle |
| 160 | Virtual detector |

The invention claimed is:
1. A method, comprising:
   generating a radiation beam that traverses an examination region and a subject therein;
   rotating the radiation source around the examination region about an axis of rotation;
   detecting radiation that traverses the examination region and at least a heart of the subject therein and generating image data indicative thereof;
   detecting an EKG signal, which includes a plurality of the heart cycles, for the subject;
   correlating the EKG signal with the image data;
   identifying a first plurality of time periods in a first heart cycle of the EKG signal;
   identifying a second plurality of time periods in a second heart cycle of the EKG signal;
   selecting first image data for one of the time periods of the first heart cycle;
   selecting second image data for one of the time periods of the second heart cycle, wherein the first and second image data correspond to a same overlapping sub-region of the heart and a similarity measure applied to reconstructed intermediate images generated therefrom is minimized; and
   reconstructing an image based on the first and second image data.

2. The method as claimed in claim 1, wherein the selected one of the time periods of the first heart cycle is a first predetermined time period having a predetermined location within the first heart cycle and the selected one of the time periods of the second heart cycle is a second predetermined time period having a predetermined location within the second heart cycle and the predetermined width; and
   further including:
   i) generating a first intermediate image based on image data from the first predetermined time period;
   ii) generating a second intermediate image based on image data from the second predetermined time period;
   iii) determining a similarity value indicative of a similarity between the first and second intermediate images; and
   iv) modifying the width and/or the location of the second predetermined time period within the second heart cycle if the similarity value does not satisfy a predetermined criterion.

3. The method as claimed in claim 2, further including repeating ii) to iv) until the similarity value satisfies the predetermined criterion.

4. The method as claimed in claim 2, wherein the predetermined criterion is satisfied when the similarity value falls below a predetermined similarity threshold.

5. The method of claim 2, wherein the modification reduces motion between the intermediate images relative to a motion prior to the modification.

6. The method as claimed in claim 1, wherein determining the similarity value includes:
   dividing the subregion into several subdivision regions;
   subtracting an image value of a subdivision region from the one intermediate image from an image value of the same subdivision region from the other intermediate image for each subdivision region to form a respective absolute difference; and
   summing the absolute differences to generate the similarity value.

7. The method of claim 6, wherein a first of the two intermediate images is reconstructed with data only from one of the different periods and a second of the two intermediate images is reconstructed with data only from the other of the different periods.

8. The method of claim 6, wherein each region corresponds to a different voxel.

9. The method as claimed in claim 1, wherein reconstructing the images includes reconstructing the images using a weighted reconstruction algorithm.

10. The method as claimed in claim 1, wherein reconstructing the images includes reconstructing the images via filtered back-projection.

11. The method as claimed in claim 1, wherein the intermediate images are reconstructed with a lower spatial resolution than the image.

12. The method as claimed in claim 1, wherein a heart cycle spans two adjacent R-peaks of the EKG signal.

13. A computer readable storage medium encoded with instructions that when executed by a computer cause the computer to perform the method as claimed in claim 1.

14. The method of claim 1, wherein the intermediate images respectively are reconstructed with image data exclusively from a single heart cycle.

15. The method of claim 1, further comprising:
   identifying a third plurality of time periods in a third heart cycle of the EKG signal;
   selecting third image data for one of the time periods of the third heart cycle, wherein a similarity measure applied to reconstructed intermediate images generated with the second and the third image data is minimized; and
   reconstructing an image based on the first, second and third image data.

16. A computer tomograph, comprising:
   a radiation source that generates a radiation beam that traverses an examination region and at least a heart of a subject therein, wherein the radiation source rotates around the examination region about
   an axis of rotation;
   a detector unit that detects radiation traversing the examination region and generates projection data indicative thereof;
   an electrocardiograph that generates an EKG signal including a plurality of the heart cycles for the subject;
   a reconstruction unit that reconstructs an image of the subject with first and second sub-sets of projection data from two different heart cycles; wherein the sub-sets correspond to a same overlapping sub-region of the heart and a similarity measure applied to reconstructed intermediate images generated therefrom is minimized.

17. The method of claim 16, wherein the reconstruction unit reconstructs the image with three or more sub-sets of projection data respectively from three or more different heart cycles, and a similarity measure applied to intermediate images reconstructed with the three or more sub-sets of projection data is minimized.

18. The method of claim 16, wherein a location of a reconstruction window of the second sub-set of projection data within a second heart cycle of the different heart cycles is changed prior to reconstruction based on the similarity measure.

19. The method of claim 16, wherein a width of a reconstruction window for the second sub-set of projection data is changed prior to reconstruction based on the similarity measure.

20. A computer tomography method having the following steps:

a) generation by a beam source of a beam bundle passing through a periodically moving object;
b) generation of a relative movement between the beam source on the one hand and the object on the other hand, which comprises a rotation about an axis of rotation;
c) acquisition by means of a detector unit, during the relative movement, of measured values that are dependent on the intensity in the beam bundle on the other side of the object, an acquisition time being allocated to each measured value and to the beam causing the respective measured value;
d) detection of a movement signal depending on the movement of the object by means of a movement-detection device and determination of periods of the periodic movement by means of the detected movement signal;
e) reconstruction of a computer tomography image of the object from the measured values, wherein only measured values whose acquisition times lie within the periods in time intervals are used, which are so determined that a similarity measure applied to intermediate images of a same subregion of the object is minimized, wherein different intermediate images are reconstructed using measured values from time intervals from different periods;

wherein initially in each case a time interval having a pre-determinable interval width is arranged at a pre-determinable interval position in each period, in that each period forms a respective period pair with a chronologically immediately preceding period and a chronologically immediately following period, and in that for each period pair the following steps are carried out:

i) determination of a subregion of the object, which is traversed both by beams whose acquisition instants lie in the time interval of the one period and by beams whose acquisition instants lie in the time interval of the other period;
ii) generation of a first intermediate image by reconstruction of the subregion exclusively using measured values whose acquisition instants lie in the time interval of the one period;
iii) generation of a further intermediate image by reconstruction of the subregion exclusively using measured values whose acquisition instants lie in the time interval of the other period;
iv) determination of a similarity value by applying a similarity measure to the first and the further intermediate image; and
v) modifying the interval width and/or the interval position of the time interval of the other period, and repetition of the steps iii) to v) until a break-off criterion dependent on the similarity value is satisfied.

* * * * *